(12) United States Patent
Hardee et al.

(10) Patent No.: US 10,632,369 B2
(45) Date of Patent: Apr. 28, 2020

(54) METHOD TO ADJUST AVATAR ATTRIBUTES USING FITNESS METRICS

(71) Applicant: International Business Machines Corporation, Armonk, NY (US)

(72) Inventors: Christopher J. Hardee, Raleigh, NC (US); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 51 days.

(21) Appl. No.: 15/172,659

(22) Filed: Jun. 3, 2016

(65) Prior Publication Data

US 2017/0352179 A1 Dec. 7, 2017

(51) Int. Cl.
| | |
|---|---|
| *A63F 13/25* | (2014.01) |
| *G06F 3/01* | (2006.01) |
| *H04M 1/725* | (2006.01) |
| *A61B 5/00* | (2006.01) |
| *A61B 5/11* | (2006.01) |
| *G09B 19/00* | (2006.01) |
| *A63F 13/65* | (2014.01) |
| *A63F 13/211* | (2014.01) |

(Continued)

(52) U.S. Cl.
CPC .............. *A63F 13/25* (2014.09); *A61B 5/1118* (2013.01); *A61B 5/6801* (2013.01); *A61B 5/6895* (2013.01); *A61B 5/6896* (2013.01); *A61B 5/744* (2013.01); *A61B 5/7475* (2013.01); *A63F 13/211* (2014.09); *A63F 13/212* (2014.09); *A63F 13/352* (2014.09); *A63F 13/65* (2014.09); *G06F 3/011* (2013.01); *G09B 19/0038* (2013.01); *H04M 1/725* (2013.01); *A61B 5/0022* (2013.01); *A61B 5/0077* (2013.01); *A61B 5/1114* (2013.01); *A61B 2503/10* (2013.01); *A61B 2503/12* (2013.01); *A61B 2505/09* (2013.01); *A61B 2562/0219* (2013.01)

(58) Field of Classification Search
CPC .................................................. G06F 19/3481
USPC ........................................................ 345/473
See application file for complete search history.

(56) References Cited

U.S. PATENT DOCUMENTS

| | | | |
|---|---|---|---|
| 8,868,377 B2 | 10/2014 | Yuen et al. | |
| 2009/0309891 A1* | 12/2009 | Karkanias ........... | G06F 19/3418 345/581 |

(Continued)

*Primary Examiner* — Shivang I Patel
(74) *Attorney, Agent, or Firm* — Scully, Scott, Murphy & Presser, P.C.; Kristofer L. Haggerty, Esq.

(57) ABSTRACT

A method is disclosed including receiving from a user a request to associate an avatar in a computer-implemented virtual world with a wearable device, creating an association between the avatar and the wearable device in response to the request, and receiving from the wearable device activity metric data for the user generated by a sensor of the wearable device. The activity metric data is generated by the wearable device in response to the wearable device sensing the user performing an activity. The method further including determining based on the received activity metric data a type of the sensed activity, determining at least one attribute of the avatar that corresponds to the determined type of the activity, determining an amount to adjust the at least one attribute based on the received activity metric data, and adjusting the determined at least one attribute of the avatar by the determined amount.

20 Claims, 3 Drawing Sheets

(51) Int. Cl.
*A63F 13/212* (2014.01)
*A63F 13/352* (2014.01)

(56) References Cited

U.S. PATENT DOCUMENTS

| | | | |
|---|---|---|---|
| 2012/0315987 A1* | 12/2012 | Walling | A63F 13/10 463/31 |
| 2014/0141865 A1 | 5/2014 | Tropper et al. | |
| 2015/0005912 A1 | 1/2015 | Tropper et al. | |
| 2015/0037771 A1* | 2/2015 | Kaleal, III | G09B 5/02 434/257 |
| 2015/0118657 A1* | 4/2015 | Shrake | G09B 19/0092 434/127 |
| 2017/0080346 A1* | 3/2017 | Abbas | A62F 13/825 |

* cited by examiner

METHOD TO ADJUST AVATAR ATTRIBUTES USING FITNESS METRICS

FIELD

The present application relates generally to the wearable fitness technology, and more particularly to linking fitness metrics to the attributes of an avatar in a virtual world.

BACKGROUND

Wearable technology such as those sold by Fitbit®, Garmin®, Martian®, Samsung®, Apple®, Google®, and Jawbone® provide an individual with the capability to track movements, motions, heart rate, and other exercise related data of a user. For example, the wearable technology may track a number of steps, number of reps, weight used, time of exercise, level of physical exertion, a duration of rest between reps/exercises, a duration of sleep at night, a quality of sleep at night, or other similar metrics. The wearable technology may generate data based on the tracked metrics for later use.

Virtual worlds, for example, online video games or other online systems typically allow users to create an avatar as a virtual representation of the user. Avatars provide a mechanism for the user to interact with the virtual world. For example, a user may command the avatar to walk, run, jump, fight, gather resources, craft items, or perform other similar activities in the virtual world through the use of a keyboard, mouse, touch screen, or other similar input devices. Depending on the virtual world, an avatar will often include a set of attributes that define the avatar's capabilities. For example, the avatar may include a strength attribute, a vitality attribute, an agility attribute, an intelligence attribute, a wisdom attribute, a *charisma* attribute, a speed attribute, or other similar attributes. When the avatar is commanded by a user to perform an action, the avatar's attributes may be checked by the virtual world to determine if the avatar is capable of performing the action, or whether the avatar is successful in performing the action. For example, if the user commands the avatar to attack a monster, the virtual world may check the avatar's agility attribute to determine whether the attack is a hit or a miss. If the attack is a hit, the virtual world may also check the avatar's strength attribute to determine how much damage is dealt by the avatar's attack. Other similar checks may be made by the virtual world depending on the particular command that the user issues to the avatar. In addition, the avatar's attributes may also define sub attributes of the avatar. For example, the avatar's health points may be based on the avatar's vitality attribute. An avatar with a high vitality attribute may have more health points than an avatar with low vitality. Likewise, an avatar with high strength may be able to carry more weight or items than an avatar with low strength.

BRIEF SUMMARY

The methods, systems, and computer program products described herein provide a way to link activity metric data generated by a wearable device to the attributes of an avatar in a virtual world.

In an aspect of the present disclosure, a method is disclosed including receiving from a user a request to associate an avatar in a computer-implemented virtual world with a wearable device, creating an association between the avatar and the wearable device in response to the request, and receiving from the wearable device activity metric data for the user generated by a sensor of the wearable device. The activity metric data is generated by the wearable device in response to the wearable device sensing the user performing an activity. The method may further include determining based on the received activity metric data a type of the sensed activity, determining at least one attribute of the avatar that corresponds to the determined type of the activity, determining an amount to adjust the at least one attribute based on the received activity metric data, and adjusting the determined at least one attribute of the avatar by the determined amount.

In an aspect of the present disclosure, a method is disclosed including receiving a request from a user to associate an avatar in a virtual world with the wearable device, creating an association between the avatar and the wearable device in response to the request, sensing by the wearable device the user performing an activity, generating activity metric data based on the sensed activity, and transmitting the activity metric data to the virtual world, the virtual world configured to adjust at least one attribute of the avatar based on the transmitted activity metric data.

In aspects of the present disclosure apparatus, systems, and computer program products in accordance with the above aspect may also be provided.

Further features as well as the structure and operation of various embodiments are described in detail below with reference to the accompanying drawings. In the drawings, like reference numbers indicate identical or functionally similar elements.

DETAILED DESCRIPTION

Figure 1:
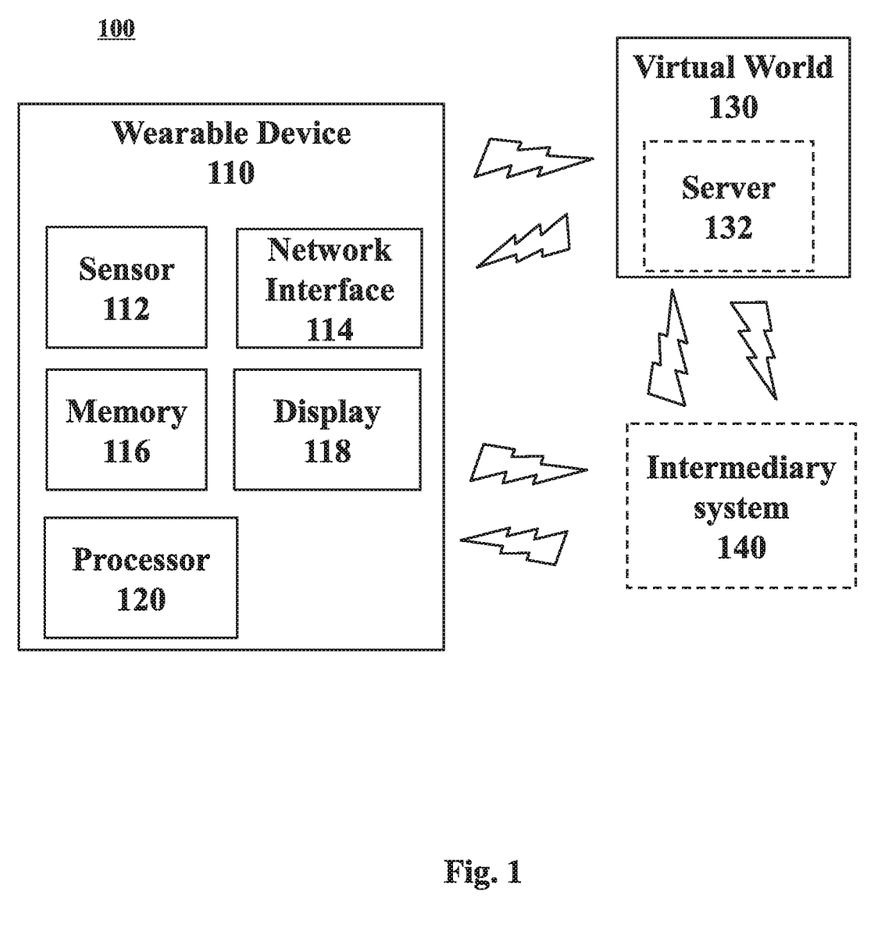
FIG. 1 is a system diagram of a linking system for linking activity metrics of a user sensed by a wearable device to the attributes of an avatar in a virtual world in accordance with an embodiment of the present disclosure.

With reference to FIG. 1, a system 100 for linking activity metrics of a user sensed by a wearable device to the attributes of an avatar in a virtual world is disclosed. Non-limiting examples of activity metrics may include a number of steps taken by the user, a distance traveled by the user, a number of calories burned by the user, a number of floors or elevation amount climbed/descended by the user, a pace of the user, a duration that the user has performed the activity, a duration that the user has been inactive, a heart rate of the user, a type of exercise performed by the user, an amount of reps performed by the user, a weight used to perform the reps, a duration of rest between reps, an intensity at which the user performs the activity, a location of the user, a duration of sleep at night, a quality of sleep at night, or other similar exercise or activity related metrics that may be tracked by a wearable device.

In some aspects, activity metrics may also include dietary information of the user. For example, wearable device 110 may be used to track the dietary information of foods and/or drinks ingested by the user. In some aspects, the user may input the dietary information of the foods and drinks into wearable device 110. In some aspects, the user may input dietary information of the foods and drinks via intermediary system 140.

In some embodiments, activity metrics may include the user's weight, an amount of weight gained, an amount of weight lost, or other similar information. For example, the user may input the user's weight into wearable device 110 or via intermediary system 140. In some embodiments, wearable device 110 may connect with a weighing device (not shown) via network interface 114 and receive data from the weighing device (not shown) including the user's weight. For example, the weighing device (not shown) may include wireless communications for communicating with wearable device 110 and/or intermediary system 140.

In some embodiments, the activity metric data may also include biometric data of the user that is sensed by a wearable device 110. For example, activity metric data may include blood pressure, heart rate, or other similar biometric data sensed by wearable device 110.

System 100 includes a wearable device 110, a virtual world 130, and in some embodiments an intermediary system 140.

Wearable Device

Wearable device 110 may include but is not limited to, for example, bracelets, armbands, headbands, buttons, scarf, belts, footwear, gloves, mobile phones, smart phones, smart watches, or any other articles or devices that may be attached, adhered to or otherwise positioned on a user. Wearable device 110 may include one or more sensors 112 that are configured to track a user's activities and to generate activity metric data for the user's activities. Some non-limiting examples of wearable devices 110 may include Vivofit® wearable devices sold by Garmin®, Fitbit® wearable devices sold by Fitbit®, a variety of smart watches sold by Martian®, Gear™ wearable devices sold by Samsung®, the Apple Watch® sold by Apple®, android Wear™ wearable devices sold by Google®, and the UP® wearable devices sold by Jawbone®.

Wearable device 110 may include a network interface 114 that is configured to transmit and receive data or other information to and from virtual world 130, the internet, a server, or any other similar system. Network interface 114 may be configured for wired or wireless communication via, for example, Bluetooth, WIFI, cellular technology, GPS, optical, satellite, or any other kind of wired or wireless communication technology.

In some aspects, wearable device 110 may include memory 116 that is configured to store activity metric data generated by sensors 112 for later use by wearable device 110 or for transmission via network interface 114 to computing device 130, the internet, a server, or any other similar system. In some aspects, historic activity metric data of the user generated from past activities may be stored in memory 116 for later use. For example, historic activity metric data may be compared to the activity metric data that is generated by sensors 112 during an activity to determine if the user has improved at the activity.

In some aspects, wearable device 110 may include a display 118 that is configured to display data related to one or more of the activity metrics. For example, display 118 may display the user's heart rate, the number of steps taken in a given period of time, or any other activity metric that is sensed by sensors 112 and/or stored in memory 116.

In some aspects, wearable device 110 may include at least one processor 120 that is operable to implement the above described features of wearable device and facilitate communication and processing with and between sensors 112, network interface 114, memory 116, and display 118.

Intermediary System

In some aspects, wearable device 110 may communicate with virtual world 130 via one or more intermediary systems 140, for example, via the internet, one or more access points, or other similar intermediary systems. For example, in some aspects, wearable device 110 may be associated with an intermediary system 140 that is configured to receive and store the activity metric data from wearable device 110. Intermediary system 140 may, for example, be a web server, website, database, or other similar system that may be used to store and disseminate information. In some aspects, intermediary system 140 may be run or managed by a company or entity that sells the wearable device 110. In some embodiments, intermediary system 140 may be configured to receive activity metric data from wearable device 110, store the activity metric data in a database or memory of intermediary system 140, and transmit the activity metric data to virtual world 130.

Virtual World

Virtual world 130 may be any system that creates or provides a virtual world for use by a user. For example, virtual world 130 may be a video game that is playable by a user. Virtual world 130 may, for example, include multi-player or single player games. In some aspects, virtual world 130 may be a massive multiplayer online role playing game (MMORPG). In some aspects, virtual world 130 may be a single player game that may be implemented on a user's personal computing device. In some aspects, virtual world 130 may be implemented as part of or on a virtual reality system. Some examples of virtual reality systems may include, for example Occulus Rift® sold by Oculus VR, LLC, Samsung Gear VR® sold by Samsung Electronics Co., Ltd., Playstation VR® sold by Sony Computer Entertainment Inc., HTC Vive® sold by HTC Corporation, and other similar virtual reality systems.

In some aspects, virtual world 130 may include one or more servers 132 that are configured to implement virtual world 130. For example, users of virtual world 130 may log into servers 132 to access virtual world 130. User's may log into servers 132 via user devices, for example, personal computing devices, laptops, tablets, mobile phones, smart phones, smart wearable technology, or any other devices. Servers 132 may include at least one processor that is operable to implement virtual world 130.

User's of virtual world 130 may experience or explore virtual world 130 using avatars. Avatars may be created by a user within virtual world 130 according to rules of virtual world 130. For example, an avatar created by a user may have certain attributes according to rules of the virtual world 130. Non-limiting examples of attributes may include, for example, strength, vitality, agility, intelligence, wisdom, *charisma*, speed, health points, recovery, stamina, or other similar attributes. In some embodiments, the avatar's attributes may be static once the avatar has been created, e.g., may not be changed due to in-game actions. In some aspects, the avatar's attributes may increase as the avatar is commanded to perform various skills, actions, or abilities by the user. For example, if the user commands the avatar to chop down a tree, the avatar's strength attribute may increase during the action and/or once the action is complete. In some aspects, the avatar's attributes may also decrease, for example, if the avatar is not used for longer than a pre-determined period of time, does not perform certain kinds of actions for longer than a pre-determined period of time, or performs actions related to other attributes. For example, if a user commands their avatar to study magic spells in a library, the intelligence attribute may increase but the strength attribute may decreases due to the lack of physical activity by the avatar. The increase or decrease in the avatar's attribute may be permanent or temporary.

In some aspects, virtual world 130 may include a level system where, for example, when the avatar's level increases, the avatar's attributes may also increase. For example, if a character has a strength attribute of ten at level five and the avatar's level increases to level six, the avatar's strength attribute may increase to twelve.

Linking Activity Metric Data to Avatar Attributes

In some aspects, the attributes of a user's avatar in virtual world 130 may be linked to the activity metric data generated by the user's wearable device 110. For example, activities performed by the user while wearing the user's wearable device 110 may be tracked, activity metric data may be generated by the user's wearable device 110, and the generated activity metric data may be provided to virtual world 130 for use in adjusting or determining the user's avatar's attributes.

In some aspects, the user may link wearable device 110 to the user's avatar in virtual world 130 by, for example, associating wearable device 110 with user's avatar in the virtual world 130, providing virtual world 130 with credential information required to access activity metric data generated by wearable device 110, associating wearable device 110 with virtual world 130 on intermediary system 140, or any other method of linking or providing activity metric data generated by wearable device 110 to virtual world. For example, a user may configure a user account for virtual world 130 to access the activity and biometric readings of a fitness account associated with wearable device 110 that contains data regarding activity or biometric readings. In some aspects, more than one account for virtual world 130 may be linked to a fitness account and more than one fitness account may be linked to an account for virtual world 130. The user may link wearable device 110 to the user's avatar via a user interface provided by virtual world 130, by wearable device 110, or by intermediary system 140. For example, the user may be able to log into virtual world 130 on the user interface and activate an element to create the association between the user's avatar and wearable device 110.

In some embodiments, intermediary system 140 may also provide virtual world 130 and may already have access to activity metric data generated by a wearable device 110 associated with intermediary system 140. For example, intermediary system 140 may include a console gaming system such as, for example, XBOX® consoles sold by Microsoft Corp., Playstation® consoles sold by Sony Computer Entertainment Inc., Nintendo® consoles sold by Nintendo of America Inc., or other similar console or computer gaming systems. The console gaming system may include a wearable device, controller, motion tracker, camera, infrared sensor, or other sensor that may be configured to sense activity metrics of a user during an activity. Since the console gaming system has access to both the activity metric data generated by the associated wearable device and to a virtual world implemented on the console, console may directly link the activity metric data generated by wearable device 110 to virtual world 130. In some aspects, the console gaming system may request permission from the user to link the activity metric data to virtual world 130.

In some aspects, the activity metric data generated by wearable device 110 may be provided to virtual world 130 directly from wearable device 110, for example, via network interface 114. In some aspects, the activity metric data may be provided first to the intermediary system 140 and intermediary system 140 may provide the activity metric data to the virtual world 130.

In some aspects, the activity metric data generated by wearable device 110 may be mapped to the avatar's attributes. For example one or more of the avatar's attributes may be mapped to one or more of the activity metrics tracked by wearable device 110. For example, activity metric data generated during strength based activities may be mapped to the strength attribute of the user's avatar, activity metric data generated during cardio or conditioning activities may be mapped to the endurance attribute of the user's avatar, activity metric data generated during sleep may be mapped to the recovery attribute of the user's avatar, etc. For example, increases in a particular type of activity may be counted towards altering a corresponding attribute that is mapped to the activity.

In some aspects, a point system may be implemented where the user earns points towards improving the avatar's attributes based on an aggregate score that they have achieved with their activity. For example, the user may earn a certain number of points per activity performed. In some aspects, the points may be specific to the attribute corresponding to the activity. For example, if a user performs a strength based activity, the user may earn points that may be applied to the avatar's strength. In some aspects, the earned points may be used for any of the avatar attributes. For example, if the user performs an agility exercise, the user may earn generic points that may be applied to any attribute of the avatar, for example, to the strength of the avatar.

In some aspects, a physical appearance of the user's avatar may change based on the user's activity metric data. For example, virtual worlds often include feature customization options during avatar creation or in some case after creation of the avatar. The feature customization options allow the user to customize the look and feel of the avatar to suite their tastes. For example, the user may adjust the height, weight, muscle content, fat ratio, facial features, hair style, hair color, eye color, hip width, etc. At least some of these features may be adjusted based on the user's activity metric data. For example, the user's activity metric data may be used as a basis for adjusting features including but not limited to the weight, muscle content, fat ratio, and other similar attributes of an avatar. For example, if the user performs a cardio activity, such as running, kickboxing, or similar light weight (or no weight) high repetition type workout, the muscle tone of the user's avatar may improve or increase based on activity metric data generated by wearable device 110 for that activity. For example, if the user performs a bench press, pushup, or other similar upper body activity, the appearance of the upper body of the user's avatar may change based on the activity metric data for those activities. Similarly, if the user does not perform upper body activities for a certain period of time, e.g., a week, detecting of the lack of activity metric data for those activities may trigger a corresponding change on the upper body of the avatar.

In some aspects, changes in the avatar's features may be displayed on the display 118 of wearable device 110 in real-time for the user to see. For example, an image of the avatar may be displayed on the wearable device 110. Initially the avatar in the image may have a first physical appearance. As the user performs the activity, the physical appearance of the avatar may change from the first physical appearance to at least a second physical appearance in real-time. For example, the image of the avatar may change as the user performs the activity. In some aspects, the longer the user performs the activity, the greater the change in the physical appearance of the avatar. Likewise, an image of the avatar may be displayed on wearable device 110 even when the user is not performing the activity. For example, if the user does not perform an activity or the activity for a certain period of time the physical appearance of the avatar displayed on the user's wearable device may also change due to the lack of activity by the user. In some aspects, the image of the avatar may be alternatively or additionally be displayed and adjusted on a display of a personal computer, table, laptop, mobile phone, smart phone, television, or other similar device of the user.

In some embodiments, increases to the avatar's attributes may be based on improvements and/or regressions made by the user during the user's activities. For example, if the user performs ten push-ups during the user's activities for three weeks straight the activity metric data generated by wearable device 110 may indicate that the user has not improved. Based on this indication, the avatar's strength attribute may not be increased any further by virtual world 130 even thought the user is performing the activities. Likewise, for example, if the user reduces the number of push-ups over a three week span from ten to seven, the activity metric data generated by wearable device 110 may indicate that the user has actually regressed. Based on the indication that the user has regressed, the avatar's strength attribute may be decrease by virtual world 130. Similarly, for example, if the user increases the number of push-ups over a three week span from ten to thirteen, the activity metric data generated by wearable device 110 may indicate that the user has improved. Based on the indication that the user has improved, the avatar's strength attribute may be increased by virtual world 130. The amount of improvement or regression may be based on how much progress or regression the user has made. For example, a regression from ten to five pushups may cause a greater decrease in the strength attribute as compared to a regression from ten to eight pushups. Likewise an improvement from ten to fifteen pushups may cause a greater increase in the strength attribute as compared to an improvement from ten to twelve pushups.

When the user first links the user's virtual world account to the user's wearable device 110, a baseline of the user's condition may be generated by wearable device for use with the user's avatar. For example, during an initial period of time, the activity metric data generated by wearable device 110 may be stored to form a baseline of the user's condition. The initial period of time may be, for example, a day, a week, a month, or any other amount of time. Virtual world 130 may associate the user's baseline with the avatar's baseline attribute levels as they were initially set during creation of the avatar by the user. Once the user's baseline condition has been established and associated with the avatar's baseline attribute levels, any additional activities may be tracked by wearable device 110 and the generated activity metric data for those additional activities may be used by virtual world 130 to increase or decreases the user's avatar's attributes accordingly.

In some aspects, the amount of increase of the avatar's attribute may be based on an amount of improvement made by the user. For example, if the user performs ten pushups per push-up activity in the baseline condition and the user improves to twelve pushups per push-up activity, the avatar's attribute may be improved by a corresponding amount. For example, the avatar's strength attribute may increase from ten to twelve. In some aspects, the avatar's attribute may proportionately increase by the amount of improvement. For example, an increase in the number of push-ups of twenty percent may cause a corresponding increase in the attribute by twenty percent.

In some aspects, virtual world 130 may provide attribute increases and decreases as a bonus or penalty based on the activity metric data. For example, if the user performs or does not perform an activity and activity metric data is generated by wearable device 110, the user may receive a bonus or penalty that may be applied to the avatar's attributes. In some embodiments, virtual world 130 may provide wearable device 110 or intermediary system 140 with specific achievements that the user may attempt to accomplish. For each achievement that the user accomplishes, one or more of the avatar's attributes may be increased by virtual world 130. In some aspects the increases may be permanent. In some aspects the increases may be temporary, for example, an attribute increase may last an hour, a day, week, only for the next play session, or any other similar amount of time.

In some aspects, virtual world 130 or intermediary system 140 may generate a workout plan that may allow a user to maximize increases to specific avatar's attributes. For example, the workout plan may target certain parts of the user's body or the user's cardiopulmonary system to achieve maximal gains in those areas and maximum increases to the corresponding avatar attributes. In some aspects the workout plan may also provide the user with a countdown timer that indicates a time remaining for the user to perform an exercise before the avatar attributes revert or regress. For example, the countdown timer may indicate that the user has two hours left before an attribute increase is removed. In some aspects, there may be a separate countdown timer for each activity and/or attribute.

In some aspects, workout plan may provide an indication to the user of which attributes of the avatar are available for increases and the types of activities that are mapped to those attributes. In some aspects, a list of workouts may be generated that correspond to the types of activities that are mapped to the attributes that are available for increases.

In some aspects, virtual world 130 may only allow the user to cumulatively increase the attributes of the user's avatar up to a maximum benefit level. For example, virtual world 130 may limit the amount that the avatar's attributes may be increased due to activities tracked by wearable device 110. For example, in some aspects, the avatar's strength attribute may only be able to be increased based on activity metric data from wearable device 110 by a total of five points. In some aspects, if an adjustment to the attribute would increase the attribute more than the maximum benefit level, the adjustment may be capped to the maximum benefit level. In some embodiments, the maximum benefit level may be spread across the avatar's attributes. For example, the maximum benefit level may be limited to an increase of five points total regardless of which attribute is increases. For example, if there are both increases in strength and agility, the combined increase may be limited to five points, e.g., three points in strength and two points in agility. In some aspects, virtual world 130 may limit the amount that each activity type may increase a particular attribute. For example, virtual world may allow an increase of two points based on a push-up activity, two points based on a pull-up activity, two points based on a squat activity, etc. In this manner, virtual world 130 ensures that the user performs a variety of activities to achieve the desired attribute increases. For example, the attribute increase based on a running activity may be capped out while the user may still perform a weight lifting activity to achieve attribute increases.

In some aspects, the attributes of the avatar may be displayed on display 118 of wearable device 110 in real-time. For example, the strength attribute may be displayed on display 118 of wearable device 110 for the user to see during the activity. As the user performs the activity, the value of avatar attributes displayed on the display 118 of wearable device 110 may be adjusted in real-time. For example, the strength attribute may have an initial value of ten. As the user performs an activity, for example, a bench press, the displayed value of the strength attribute may increase, for example, to eleven. If the user continues to perform the activity or another strength related activity, the displayed strength attribute may further increase to, for example, twelve. In some aspects, the initial value of the attribute may always be displayed for the user and any adjustments to the attribute may be displayed by an adjustment indicator. For example, if the strength attribute has increased by two, the adjustment indicator may be displayed as the initial value of ten plus and adjustment value of two. For example, the strength attribute with adjustment indicator may be displayed on wearable device as "10+2". In some aspects, the adjustment indicator may include a color coding, for example, the color green for increases to the attribute, the color orange for no change to the attribute, and the color red for decreases to the attribute. In some aspects, the attributes of the avatar may be displayed on wearable device 110 even when the user is not performing the activity. For example, if the user does not perform an activity for a certain period of time the attributes of the avatar displayed on the user's wearable device may also be adjusted in real-time. For example, the strength attribute of the avatar displayed on wearable device 110 may be decreases over time due to the lack of activity by the user. In some aspects, attributes of the avatar may be alternatively or additionally be displayed and adjusted on a display of a personal computer, table, laptop, mobile phone, smart phone, television, or other similar device of the user.

In some aspects, the user may be presented on display 118 with a preview of any adjustments to the avatar's attributes or physical appearance that would be achieved by the user performing a particular activity or achieving a particular achievement. For example, prior to engaging in the activity, the user may preview the adjustment to the avatar's attributes and physical appearance by selecting the activity or achievement on the wearable device 110. The preview may, for example, present the current attribute and/or physical appearance and may also or alternatively present the attribute or physical appearance as it would be adjusted should the user perform the activity or achieve the achievement. For example, if the user selects a bench press activity or achievement on the wearable device 110, a preview of the attribute increase may be presented to the user. For example, wearable device 110 may indicate to the user that the strength attribute would increase from ten to twelve if the user performs the bench press activity.

In some aspects, wearable device 110 may present a warning to the user that the attributes and/or physical appearance of the avatar will be adjusted if the user does not perform an activity or achieve an achievement within a pre-determined period of time. The warning may be visual, audio, and/or tactile. In some aspects, in addition to the warning, wearable device 110 may also present a preview of the adjustment that will be made if the user does not perform the activity or achieve the achievement. For example, if the pre-determined period of time is twenty-four hours, a warning may be issued prior to the twenty-four hour mark to inform the user that an adjustment is pending and may present a preview of the adjustment, for example, adjusting the strength attribute from ten to eight. In some aspects, multiple warnings may be issued to the user by wearable device 110. For example, a warning may be issued one hour before the pre-determined period expires, thirty minutes before the pre-determine period expires, five minutes before the pre-determined period expires, or other similar times.

Figure 2:
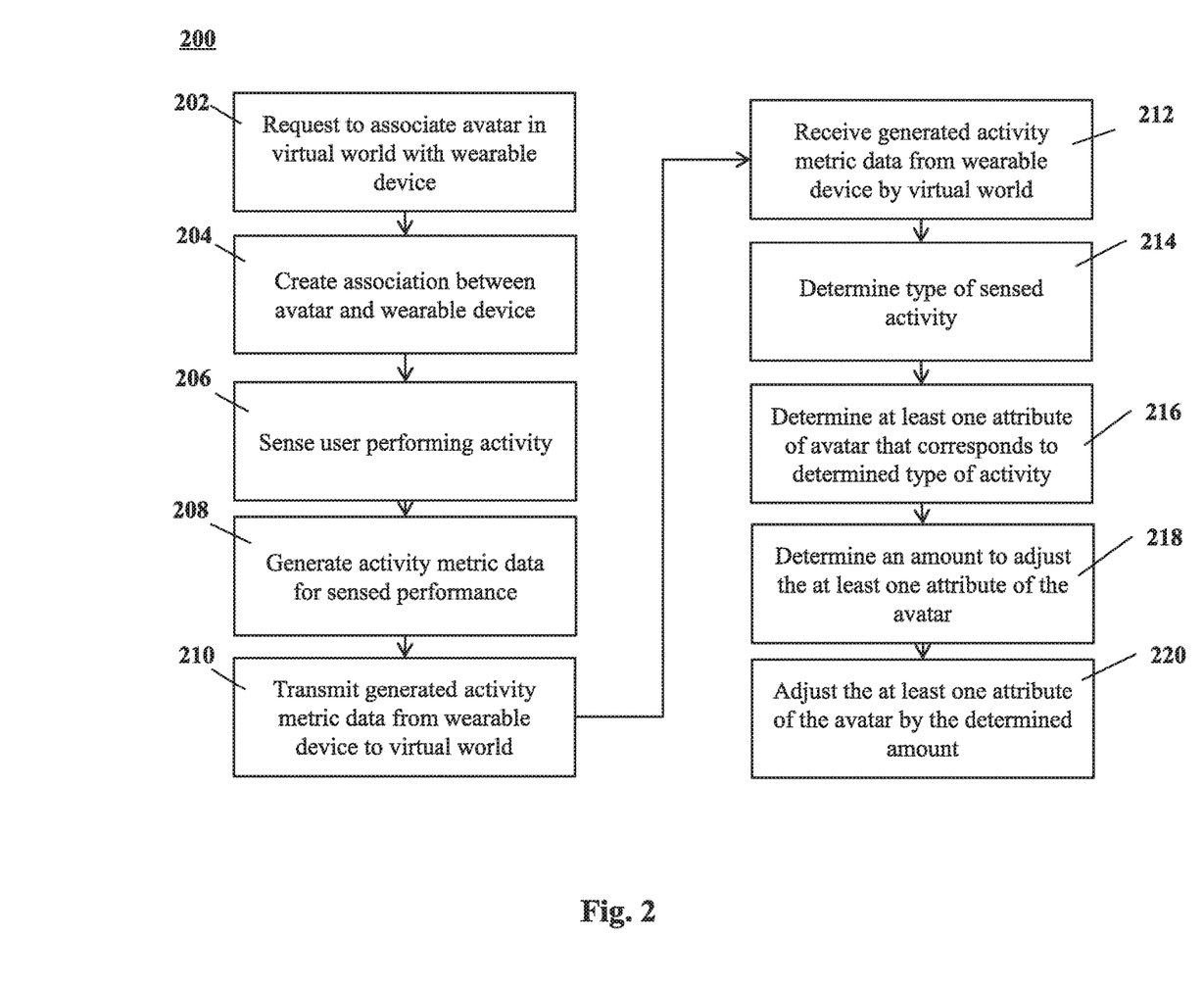
FIG. 2 is a flow chart illustrating an example method of linking activity metrics of a user sensed by a wearable device to the attributes of an avatar in a virtual world in accordance with an embodiment of the present disclosure.

With reference to FIG. 2, a method 200 of linking a wearable device to an avatar is disclosed. At 202, a request is submitted by a user to any or all of wearable device 110, virtual world 130, and/or intermediary system 140 requesting that the user's avatar be associated with the wearable device 110. At 204, in response to the request, an association between the user's avatar and the wearable device is created. For example, the association may be created by wearable device 110, virtual world 130, and/or intermediary system 140. At 206, sensors 112 on wearable device 110 sense that the user is performing an activity. At 208, wearable device 110 generates activity metric data for the sensed performance of the activity. At 210, wearable device 110 transmits the activity metric data to virtual world 130. In some embodiments, wearable device 110 may transmit the activity metric data to intermediary system 140. In some embodiments intermediary system 140 may transmit the activity metric data to virtual world 130. At 212, virtual world 130 receives the generated activity metric data either from wearable device 110 directly or via intermediary system 140. At 214, virtual world 130 determines a type of the sensed activity based on the received activity metric data. At 216, virtual world 130 determines at least one attribute of the avatar that corresponds to the determined type of sensed activity. For example, if the sensed activity is the bench press, virtual world 130 may determine that the bench press corresponds to the avatar's strength attribute. At 218, virtual world 130 determines an amount to adjust the at least one attribute of the avatar. For example, virtual world 130 may determine that the at least one attribute of the avatar needs to be increased by two points based on the user's performance of the activity. The determination may, for example, be made based on the amount of time that the user performs the activity, a number of reps of the activity, an amount of weight used in the activity, an intensity level of the activity or other similar metrics. In some aspects, the amount may be proportional to a level of improvement made by the user as compared to historic performance of the activity. For example, if the user has performed two more push-ups than normal, the amount of adjustment to the attribute may be increased proportionately. At 220, the at least one attribute of the avatar is adjusted by the determined amount.

In an aspect of the present disclosure, a method is disclosed including receiving from a user a request to associate an avatar in a virtual world with a wearable device, creating an association between the avatar and the wearable device in response to the request, and receiving from the wearable device activity metric data for the user. The activity metric data is generated by the wearable device in response to the wearable device sensing the user performing an activity. The method may further include determining based on the received activity metric data a type of the sensed activity, determining at least one attribute of the avatar that corresponds to the determined type of the activity, determining an amount to adjust the at least one attribute based on the received activity metric data, and adjusting the determined at least one attribute of the avatar by the determined amount.

In an aspect, the activity metric data may include at least one of duration of the activity, the type of the activity, an intensity at which the user performed the activity, an amount that the user has improved in the activity, an amount of weight that the user has gained or lost, an amount of sleep that the user receives each night, and a diet of the user.

In some aspects, historical activity metric data may be stored in a memory of the wearable device. The method may include comparing the historical activity metric data to the activity metric data and based on the comparison, determining that the user's performance of the activity has improved. The determined amount may be based at least in part on the determination that the user's performance of the activity has improved.

In another aspect, the method may include determining an amount that the user has improved based on the comparison. The determined amount to adjust the at least one attribute may be proportionate to the amount that the user has improved.

In yet another aspect, the at least one attribute may include at least one of health points, recovery, stamina, speed, strength, and agility.

In an aspect, the at least one attribute may include the avatar's physical appearance.

In some aspect, the method may include in response to creating the association between the avatar and the wearable device, establishing a baseline of the user's condition and a corresponding baseline of the avatar's attributes. The baseline of the user's condition may be based on activity metric data generated by the wearable device for a pre-determined period of time.

In another aspect, the method may include generating a workout plan that is configured to maximize increases to at least one specific attribute of the avatar, transmitting the workout plan to the wearable device, the wearable device configured to present the workout plan to the user, receiving activity metric data from the wearable device corresponding to the user performing the workout plan, and adjusting the at least one specific attribute of the avatar by a maximum amount in response to receiving the activity metric data corresponding to the user performing the workout plan.

In yet another aspect, the method may include establishing a maximum amount of adjustment allowed for at least one of the attributes, determining that the amount to adjust the at least one attribute would adjust the at least one attribute more than the maximum amount of adjustment allowed, and capping the amount of adjustment allowed to the maximum amount.

Figure 3:
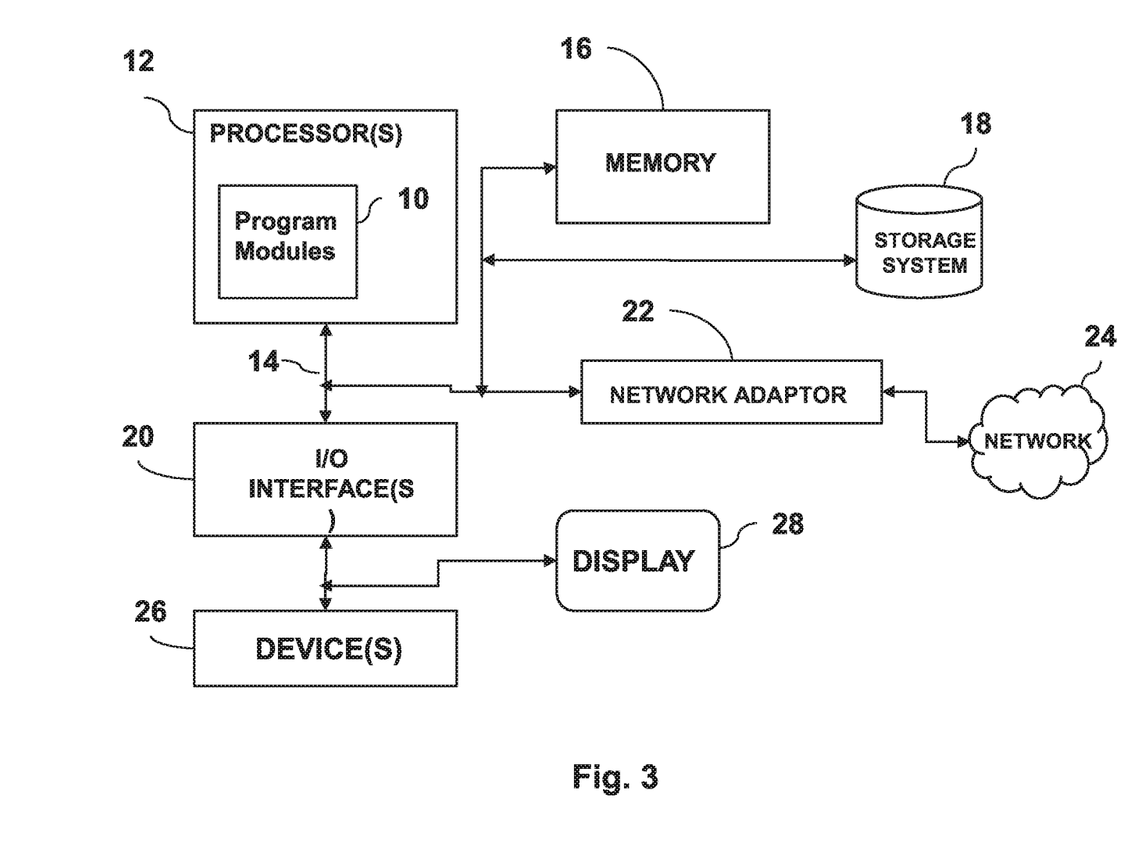
FIG. 3 illustrates a schematic of an example computer or processing system that may implement a linking system in accordance with an embodiment of the present disclosure.

FIG. 3 illustrates a schematic of an example computer or processing system that may implement any of wearable device 110, virtual world 130, and intermediary system 140 in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the system shown in FIG. 1 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of the computer system may include, but are not limited to, one or more processors or processing units 12, a system memory 16, and a bus 14 that couples various system components including system memory 16 to processor 12. The processor 12 may include one or more program modules 10 that perform the methods described herein. The program modules 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages, a scripting language such as Perl, VBS or similar languages, and/or functional languages such as Lisp and ML and logic-oriented languages such as Prolog. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The computer program product may comprise all the respective features enabling the implementation of the methodology described herein, and which—when loaded in a computer system—is able to carry out the methods. Computer program, software program, program, or software, in the present context means any expression, in any language, code or notation, of a set of instructions intended to cause a system having an information processing capability to perform a particular function either directly or after either or both of the following: (a) conversion to another language, code or notation; and/or (b) reproduction in a different material form.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Various aspects of the present disclosure may be embodied as a program, software, or computer instructions embodied in a computer or machine usable or readable medium, which causes the computer or machine to perform the steps of the method when executed on the computer, processor, and/or machine. A program storage device readable by a machine, tangibly embodying a program of instructions executable by the machine to perform various functionalities and methods described in the present disclosure is also provided.

The system and method of the present disclosure may be implemented and run on a general-purpose computer or special-purpose computer system. The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, and/or server. A module may be a component of a device, software, program, or system that implements some "functionality", which can be embodied as software, hardware, firmware, electronic circuitry, or etc.

The embodiments described above are illustrative examples and it should not be construed that the present invention is limited to these particular embodiments. Thus, various changes and modifications may be effected by one skilled in the art without departing from the spirit or scope of the invention as defined in the appended claims.

What is claimed is:

1. A method performed by at least one processor, comprising:
   receiving from a user a request to associate an avatar in a computer-implemented virtual world with a wearable device, wherein the avatar includes a set of attributes defining capabilities of the avatar to perform actions in the virtual world;
   creating an association between the avatar and the wearable device in response to the request;
   generating, by the computer-implemented virtual world, a workout plan for the user that is configured to increase at least one specific attribute among the set of attributes of the avatar in the virtual world, the workout plan indicating mappings between physical activities detectable by the wearable device and the set of attributes of the avatar, wherein an attribute being mapped to a physical activity indicates that the user performing the physical activity leads to an increase of a level of the attribute in the virtual world;
   transmitting the workout plan to the wearable device, the wearable device configured to present the workout plan to the user including presenting to the user the mappings between physical activities and the set of attributes of the avatar;
   receiving activity metric data from the wearable device, the activity metric data generated by a sensor coupled to the wearable device, the activity metric data generated by the wearable device in response to the wearable device detecting the user performing a physical activity among the mappings indicated by the workout plan;
   determining based at least in part on the activity metric data that the user has performed a particular physical activity mapped to a particular attribute of the avatar in the workout plan; and
   adjusting the particular attribute of the avatar in the virtual world in response to determining that the user has performed the particular physical activity mapped to the particular attribute of the avatar in the workout plan, wherein an amount of the adjustment is based on the activity metric data, and the adjustment causes the avatar to perform a particular action in the virtual world using the particular attribute at an increased level in accordance with the amount of the adjustment.

2. The method of claim 1, wherein the activity metric data comprises at least one of duration of the particular physical activity, the type of the particular physical activity, an intensity at which the user performed the particular physical activity, an amount that the user has improved in the particular physical activity, an amount of weight that the user has gained or lost, an amount of sleep that the user receives each night, and a diet of the user.

3. The method of claim 1,
   wherein historical activity metric data is stored in a memory associated with the wearable device;
   wherein adjusting the particular attribute of the avatar in response to determining that the user has performed the particular physical activity mapped to the particular attribute of the avatar in the workout plan comprises:
   comparing the historical activity metric data to the activity metric data;
   determining, based at least in part on the comparison of the historical activity metric data to the activity metric data, an amount that the user has improved or regressed in performance of the particular physical activity mapped to the particular attribute of the avatar in the workout plan;

determining an amount to adjust the particular attribute based at least in part on the determined amount that the user has improved or regressed in the performance of the particular physical activity mapped to the particular attribute of the avatar in the workout plan; and adjusting the particular attribute by the determined amount to adjust the particular attribute.

4. The method of claim 3, wherein the determined amount to adjust the particular attribute is proportionate to the determined amount that the user has improved or regressed in the performance of the particular physical activity mapped to the particular attribute of the avatar in the workout plan.

5. The method of claim 1, wherein the particular attribute includes at least one of the avatar's physical appearance, health points, recovery, stamina, speed, strength, and agility in the virtual world.

6. The method of claim 1, further comprising:
in response to creating the association between the avatar and the wearable device:
establishing a baseline of the user's condition and a corresponding baseline of the avatar's attributes, wherein the baseline of the user's condition is based on activity metric data generated by the wearable device for a pre-determined period of time.

7. The method of claim 1,
wherein the workout plan is configured to maximize increases to the at least one specific attribute of the avatar, and
wherein adjusting the particular attribute of the avatar comprises adjusting the particular attribute by a pre-determined maximum amount in response to receiving the activity metric data corresponding to the user performing the particular physical activity mapped to the particular attribute of the avatar in the workout plan.

8. The method of claim 1, further comprising:
establishing a maximum amount of adjustment allowed for the particular attribute;
determining that an amount to adjust the particular attribute would adjust the particular attribute more than the maximum amount of adjustment allowed; and
capping the amount to adjust the particular attribute to the maximum amount.

9. The method of claim 1, further comprising
receiving a selection of a physical activity from the workout plan by the user; and
in response to receiving the selected physical activity from the workout plan, presenting, on a display, a preview of the increase to an attribute of the avatar mapped to the selected physical activity that would occur in response to the user performing the selected physical activity.

10. The method of claim 1, wherein the virtual world is a video game.

11. A system comprising:
at least one processor operable to:
receive from a user a request to associate an avatar in a virtual world with a wearable device, wherein the avatar includes a set of attributes defining capabilities of the avatar to perform actions in the virtual world;
create an association between the avatar and the wearable device in response to the request;
generate, by the virtual world, a workout plan for the user that is configured to increase at least one specific attribute among the set of attributes of the avatar in the virtual world, the workout plan indicating mappings between physical activities detectable by the wearable device and the set of attributes of the avatar, wherein an attribute being mapped to a physical activity indicates that the user performing the physical activity leads to an increase of a level of the attribute in the virtual world;
transmit the workout plan to the wearable device, the wearable device configured to present the workout plan to the user including presenting to the user the mappings between physical activities and the set of attributes of the avatar;
receive activity metric data from the wearable device, the activity metric data generated by a sensor coupled to the wearable device the activity metric data generated by the wearable device in response to the wearable device detecting the user performing a physical activity among the mappings indicated by the workout plan;
determine based at least in part on the activity metric data that the user has performed a particular physical activity mapped to a particular attribute of the avatar in the workout plan; and
adjust the particular attribute of the avatar in the virtual world in response to determining that the user has performed the particular physical activity mapped to the particular attribute of the avatar in the workout plan, wherein an amount of the adjustment is based on the metric data, and the adjustment causes the avatar to perform a particular action in the virtual world using the particular attribute at an increased level in accordance with the amount of the adjustment.

12. The system of claim 11, wherein the activity metric data comprises at least one of duration of the activity, the type of the activity, an intensity at which the user performed the activity, an amount that the user has improved in the activity, an amount of weight that the user has gained or lost, an amount of sleep that the user receives each night, and a diet of the user.

13. The system of claim 11,
wherein historical activity metric data is stored in a memory associated with the wearable device; and
wherein adjusting the particular attribute of the avatar in response to determining that the user has performed the particular physical activity mapped to the particular attribute of the avatar in the workout plan comprises:
comparing the historical activity metric data to the activity metric data;
determining, based at least in part on the comparison of the historical activity metric data to the activity metric data, an amount that the user has improved or regressed in performance of the particular physical activity mapped to the particular attribute of the avatar in the workout plan;
determining an amount to adjust the at least one specific attribute based at least in part on the determined amount that the user has improved or regressed in the performance of the particular physical activity mapped to the particular attribute of the avatar in the workout plan; and
adjusting the particular attribute by the determined amount to adjust the particular attribute.

14. The system of claim 13, wherein the determined amount to adjust the particular attribute is proportionate to the determined amount that the user has improved or regressed in the performance of the particular physical activity mapped to the particular attribute of the avatar in the workout plan.

15. The system of claim 11, wherein the particular attribute includes at least one of the avatar's physical appearance, health points, recovery, stamina, speed, strength, and agility in the virtual world.

16. The system of claim 11, wherein the at least one processor is further operable to:
in response to creating the association between the avatar and the wearable device:
establish a baseline of the user's condition and a corresponding baseline of the avatar's attributes, wherein the baseline of the user's condition is based on activity metric data generated by the wearable device for a pre-determined period of time.

17. The system of claim 11, wherein the workout plan is configured to maximize increases to the particular attribute of the avatar, and
wherein adjusting the particular attribute of the avatar comprises adjusting the particular attribute by a pre-determined maximum amount in response to receiving the activity metric data corresponding to the user performing the workout plan.

18. The system of claim 11, wherein the at least one processor is further operable to:
establish a maximum amount of adjustment allowed for the particular attribute;
determine that an amount to adjust the particular attribute would adjust the particular attribute more than the maximum amount of adjustment allowed; and
limit the amount to adjust the particular attribute to the maximum amount.

19. A method performed by at least one processor, comprising:
receiving a request from a user to associate an avatar in a virtual world with a wearable device, wherein the avatar includes a set of attributes defining capabilities of the avatar to perform actions in the virtual world;
creating an association between the avatar and the wearable device in response to the request;
receiving, from the virtual world, a workout plan for the user that is configured to increase at least one specific attribute among the set of attributes of the avatar in the virtual world, the workout plan indicating mappings between physical activities detectable by the wearable device and the set of attributes of the avatar, wherein an attribute being mapped to a physical activity indicates that the user performing the physical activity leads to an increase of a level of the attribute in the virtual world;
presenting, by the wearable device, the workout plan to the user including presenting to the user the mappings between physical activities and the set of attributes of the avatar;
detecting, by the wearable device, the user performing a particular physical activity among the mappings indicated by the workout plan, the particular physical activity being mapped to a particular attribute of the avatar;
generating activity metric data based on the detected particular physical activity;
determining based at least in part on the activity metric data that the user has performed the particular physical activity mapped to the particular attribute of the avatar in the workout plan; and
transmitting the activity metric data and an indication that the user has performed the particular physical activity to the virtual world in response to determining that the user has performed the particular physical activity, the virtual world configured to adjust the particular attribute of the avatar based on the transmitted indication that the user has performed the particular physical activity, wherein an amount of the adjustment is based on the activity metric data, and the adjustment causes the avatar to perform a particular action in the virtual world at an increased level in accordance with the amount of the adjustment.

20. The method of claim 19,
wherein the workout plan is configured to maximize increases to the at least one specific attribute of the avatar, and
wherein the virtual world is configured to adjust the at least one specific attribute of the avatar by a pre-determined maximum amount in response to receiving the transmitted indication that the user has performed the workout plan.

* * * * *